(12) United States Patent
Dunn

(10) Patent No.: US 9,788,986 B2
(45) Date of Patent: Oct. 17, 2017

(54) HINGE FOR AN ORTHOPEDIC DEVICE

(71) Applicant: OSSUR HF, Reykjavik (IS)

(72) Inventor: Adam Dunn, Laguna Niguel, CA (US)

(73) Assignee: OSSUR HF, Reykjavik (IS)

( * ) Notice: Subject to any disclaimer, the term of this patent is extended or adjusted under 35 U.S.C. 154(b) by 319 days.

(21) Appl. No.: 14/619,512

(22) Filed: Feb. 11, 2015

(65) Prior Publication Data

US 2015/0223958 A1 Aug. 13, 2015

Related U.S. Application Data

(60) Provisional application No. 61/938,243, filed on Feb. 11, 2014.

(51) Int. Cl.
*A61F 5/01* (2006.01)

(52) U.S. Cl.
CPC .......... *A61F 5/0102* (2013.01); *A61F 5/0123* (2013.01); *A61F 2005/0132* (2013.01); *A61F 2005/0139* (2013.01); *A61F 2005/0144* (2013.01); *A61F 2005/0167* (2013.01); *A61F 2005/0174* (2013.01)

(58) Field of Classification Search
CPC ............ A61F 5/0102; A61F 2005/0132; A61F 2005/0139; A61F 2005/0144; A61F 5/0123; A61F 5/0125; A61F 2005/0167
See application file for complete search history.

(56) References Cited

U.S. PATENT DOCUMENTS 3,901,223 A 8/1975 May
4,723,539 A 2/1988 Townsend
4,791,916 A 12/1988 Paez
4,821,707 A 4/1989 Audette
4,856,501 A 8/1989 Castillo et al.
(Continued)

FOREIGN PATENT DOCUMENTS

EP 0 454 186 A2 10/1991
EP 0 546 330 A1 6/1993
(Continued)

OTHER PUBLICATIONS

International Search Report from International Application No. PCT/US2015/015358, Apr. 22, 2015.
(Continued)

*Primary Examiner* — Ophelia A Hawthorne
(74) *Attorney, Agent, or Firm* — Workman Nydegger

(57) ABSTRACT

A hinge includes an upper hinge component and a lower hinge component. A cover plate is pivotally connected at first location point to the upper hinge component and at a second location point to the lower hinge component. First and second plates are pivotally connected at a third location point to the upper hinge component and at a fourth location point to the lower hinge component. The first plate is positioned between the cover plate and the upper and lower hinge components. The upper and lower hinge components are positioned between the first and second plates. The cover plate is mounted on an outer side of the hinge and the connection of the cover plate at the first location point rotates around the third location point and the connection of the cover plate at the second location point rotates around the fourth location point.

19 Claims, 5 Drawing Sheets

(56) References Cited

U.S. PATENT DOCUMENTS

| | | |
|---|---|---|
| 4,886,054 A | 12/1989 | Castillo et al. |
| 4,890,607 A | 1/1990 | Townsend |
| 4,940,044 A | 7/1990 | Castillo |
| 4,961,416 A | 10/1990 | Moore et al. |
| 5,022,391 A | 6/1991 | Weidenburner |
| 5,038,763 A | 8/1991 | Wiggins |
| 5,168,865 A | 12/1992 | Radcliffe et al. |
| 5,259,832 A | 11/1993 | Townsend et al. |
| 5,288,287 A | 2/1994 | Castillo et al. |
| 5,356,370 A | 10/1994 | Fleming |
| 5,372,572 A | 12/1994 | Tamagni |
| 5,376,134 A | 12/1994 | Biedermann |
| 5,490,822 A | 2/1996 | Biedermann |
| 5,741,221 A | 4/1998 | Wetz et al. |
| 6,074,355 A | 6/2000 | Bartlett |
| 6,740,054 B2 | 5/2004 | Stearns |
| 7,044,925 B2 | 5/2006 | Castillo et al. |
| 7,059,329 B2 | 6/2006 | Mason et al. |
| 7,235,058 B2 | 6/2007 | Doty et al. |
| 7,507,215 B2 | 3/2009 | Ryan |
| 7,534,219 B2 | 5/2009 | Stearns |
| 7,544,174 B2 | 6/2009 | Nathanson |
| 7,578,799 B2 | 8/2009 | Thorsteinsson et al. |
| 7,762,972 B2 | 7/2010 | Cho |
| 7,985,193 B2 | 7/2011 | Thorsteinsson et al. |
| 8,287,476 B2 * | 10/2012 | Bettiol .................. A61F 5/0123 602/16 |
| 2005/0148915 A1 | 7/2005 | Nathanson et al. |
| 2005/0192523 A1 * | 9/2005 | Knecht .................. A61F 5/0123 602/26 |
| 2006/0009722 A1 | 1/2006 | Seligman |
| 2006/0173392 A1 | 8/2006 | Turrini et al. |
| 2008/0108922 A1 | 5/2008 | Castillo et al. |
| 2008/0188784 A1 | 8/2008 | Ceriani et al. |
| 2009/0030356 A1 | 1/2009 | Maloney |
| 2009/0182254 A1 | 7/2009 | Cho |
| 2009/0299244 A1 | 12/2009 | Chiang et al. |
| 2010/0049108 A1 | 2/2010 | Napholz |
| 2010/0286579 A1 | 11/2010 | Bettiol |
| 2012/0059296 A1 | 3/2012 | Kompa |
| 2012/0271211 A1 | 10/2012 | Bledsoe |
| 2013/0331754 A1 | 12/2013 | Dunn et al. |

FOREIGN PATENT DOCUMENTS

| | | |
|---|---|---|
| WO | 90/14807 A1 | 12/1990 |
| WO | 2004/078078 A1 | 9/2004 |
| WO | 2009/092798 A1 | 7/2009 |

OTHER PUBLICATIONS

International Search Report and Written Opinion of the International Searching Authority from International Application No. PCT/US2013/043322, Aug. 20, 2013.

International Search Report from PCT No. PCT/US2016/059005, Jan. 5, 2017.

* cited by examiner

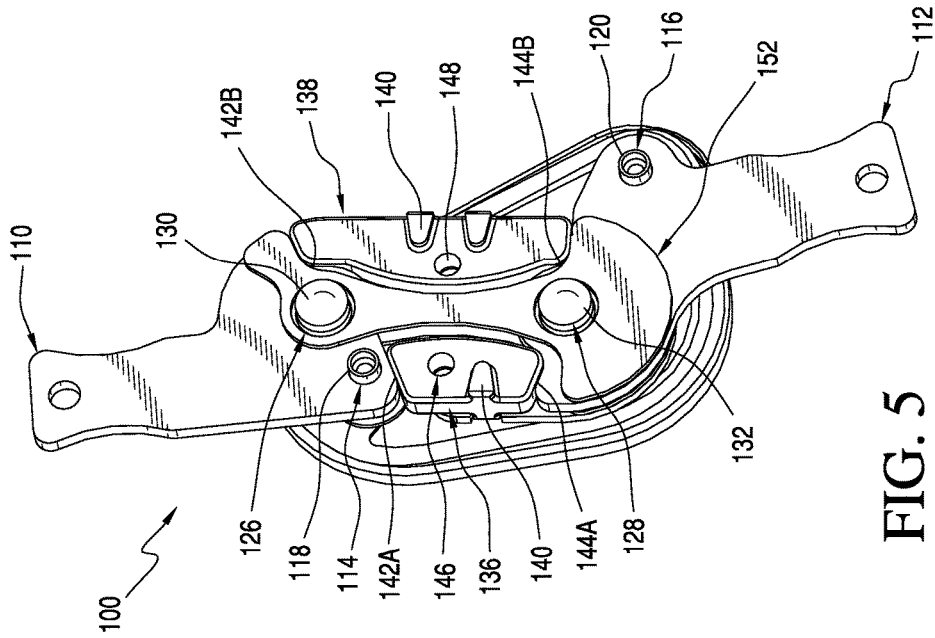
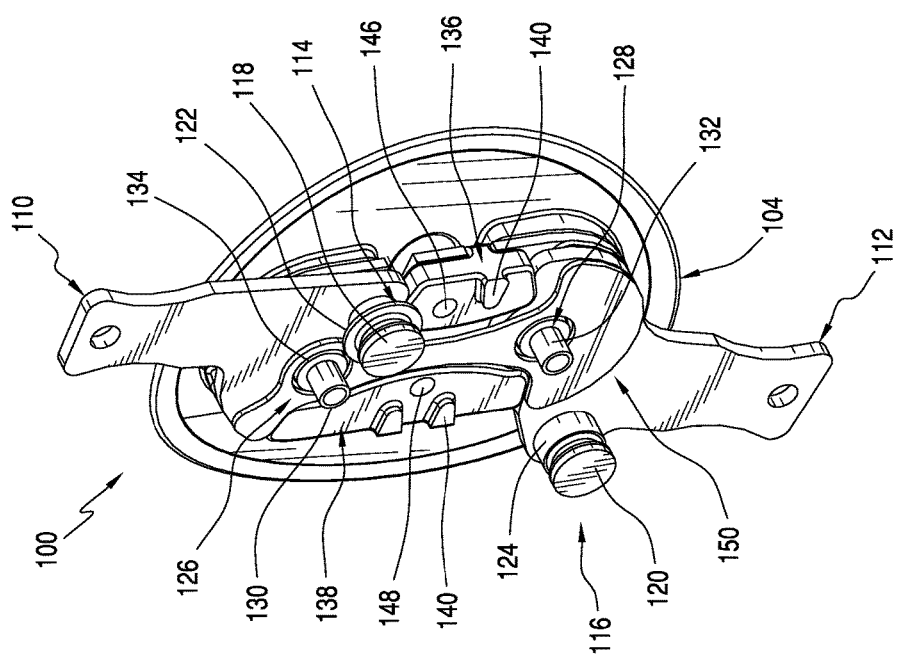
FIG. 4
FIG. 5

HINGE FOR AN ORTHOPEDIC DEVICE

TECHNICAL FIELD

The disclosure relates to a hinge for use with an orthopedic device.

BACKGROUND

Many orthopedic devices include hinges that support joints, and control and limit joint movements. These joints include the knee, elbow, shoulder, hip, ankle and wrist joints.

The knee joint comprises two joints, lateral and medial, between the femur and tibia, and one arthrodial joint between the patella and femur. The primary movements of the knee comprise flexion (i.e., rearward rotational movement of the tibia relative the femur), and extension (i.e., forward rotational movement of the tibia relative the femur).

The flexion and extension movements of the knee joint are not pivotal movements about a fixed axis. During flexion, the axis around which movement takes place shifts backward, and during extension it shifts forward. This differs from a more typical hinge joint, such as an elbow, where the axis of rotation does not shift. As full extension is reached, the tibia is rotated inward or rearward, and the joint is disposed in a "locked" position with the ligaments taut. This gives the joint greater stability in the extended position. As flexion is initiated, the tibia initially lowers or moves downwardly with small external rotation of the tibia unlocking the joint and subsequently the tibia rotates or rolls about the joint to full flexion. The initial unlocking of the knee joint during flexion precedes actual full rotation of the knee.

Because of the complexity associated with knee movement a knee brace hinge must be able to simulate the movements of the knee. Incorporating such movement into the hinge is crucial, as the knee brace must optimally support the knee joint of its user.

In postsurgical applications, the requirement for such simulation of the knee joint is essential to rehabilitate and prevent re-injury of an injured knee joint. The hinge should also control the range of the knee joint flexion and extension so the knee is not reinjured due to hyperextension or flexion. As the optimal range of knee joint motion may vary between users and change during the progress of rehabilitation, the hinge used with such surgical applications should further be adjustable to correspond to the motion range of the user's leg.

In recognizing the need for an effective postsurgical knee brace, various types of hinges have been incorporated into known knee braces for postsurgical applications. However, most conventional hinges typically fail to provide the precise simulation of knee joint movement or control the range of knee joint motion. Such deficiencies inevitably decrease the user's knee joint being properly rehabilitated after surgery.

Many known knee braces fail to provide the precise simulation of knee joint movement or have been relatively heavy, bulky apparatus, detracting from the user's mobility. Further, known designs fail to possess sufficient structural integrity to prevent re-injury of the knee joint as may be occasioned by impact to the knee joint during sport endeavors.

There is a need for an orthopedic device and hinge streamlined and low-profile, while supporting joints and controlling and limiting joint movement.

SUMMARY

The disclosure describes various embodiments of a hinge for an orthopedic device providing a construction and design that facilitates controlled movement and support of the knee, without the accompanying bulk and complexity of conventional hinges. The embodiments can provide greater support to the knee joint than conventional hinges while exhibiting a more streamlined and lower-profile design.

The embodiments described can include a hinge having an upper hinge component and a lower hinge component. A cover plate is pivotally connected at first location point to the upper hinge component and at a second location point to the lower hinge component. First and second plates are pivotally connected at a third location point to the upper hinge component and at a fourth location point to the lower hinge component. The first plate is positioned between the cover plate and the upper and lower hinge components. The upper and lower hinge components are positioned between the first and second plates. The cover plate is mounted on an outer side of the hinge and the connection of the cover plate at the first location point rotates around the third location point and the connection of the cover plate at the second location point rotates around the fourth location point. The outer side is defined as being opposed to an inner side of the hinge that is proximate the anatomy of a wearer of the orthopedic device.

The location of the cover plate on the outer side of the hinge advantageously allows the hinge to be more compact and/or streamlined because the other hinge components need not be spaced apart or oversized to accommodate movement of the cover plate during use. Because the cover plate is a single linkage rather than multiple linkages, it can also help reduce the overall thickness of the hinge. The cover plate can also both define a long linkage and protect the hinge, allowing the hinge to include fewer components, which lowers the profile of the hinge. For instance, the likelihood of the first and second plates being damaged by external objects or contact is substantially reduced because they can be protected between the cover plate and an optional condyle plate.

According to a variation, a first rotation stop is arranged to directly abut a stop surface defined on the upper and/or lower hinge component. By using the upper and lower hinge components as the contact point with the rotation stop, a stronger rotation stopping contact is formed with less opportunity for the hinge components to slip and allow further undesirable flexion or extension beyond the stopping points. Further, because the rotation stop does not directly contact the cover plate, the likelihood of the cover plate being damaged by the rotation stop is reduced.

According to a variation, the first rotation stop defines keys protruding therefrom that are arranged to be received within cutouts defined by the first and second plates. This arrangement allows the first rotation stop to transfer at least some load place on the rotation stop by the hinge components to the first and second plates, increasing the load capacity of the rotation stop. It also forms an additional connection between the first and second plates, helping the hinge to resist twisting.

BRIEF DESCRIPTION OF THE DRAWINGS

These and other features, aspects, and advantages of the present disclosure will become better understood regarding the following description, appended claims, and accompanying drawings.

FIG. 4 is a perspective view of the hinge in FIG. 1A with the cover and outer plates hidden for ease of reference.

FIG. 5 is a perspective view of the hinge in FIG. 1A with the condyle and inner plates hidden for ease of reference.

DETAILED DESCRIPTION OF VARIOUS EMBODIMENTS

Figure 1A:
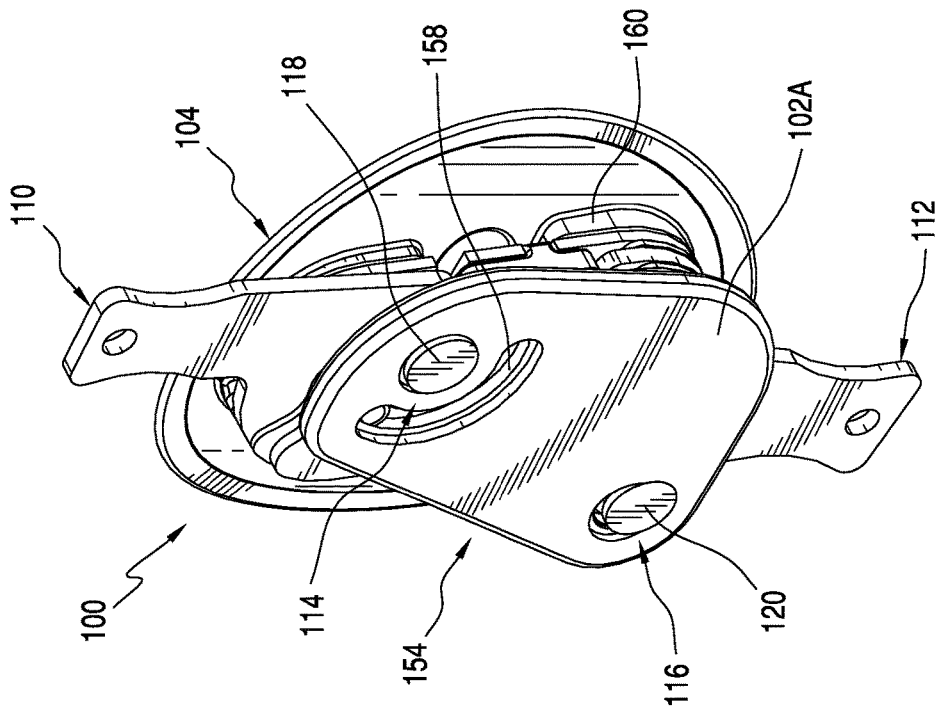
FIG. 1A is a perspective view of a hinge according to an embodiment.

A better understanding of different embodiments of the invention may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

For further ease of understanding the embodiments of an orthopedic device as disclosed, a description of a few terms is necessary. As used, the term "proximal" has its ordinary meaning and refers to a location closer to the heart than another location. Likewise, the term "distal" has its ordinary meaning and refers to a location further from the heart than another location. The term "posterior" also has its ordinary meaning and refers to a location behind or to the rear of another location. Lastly, the term "anterior" has its ordinary meaning and refers to a location ahead of or to the front of another location.

The terms "rigid," "flexible," and "resilient" may be used to distinguish characteristics of portions of certain features of the orthopedic device. The term "rigid" should denote that an element of the device is devoid of flexibility. The term "flexible" should denote that features are capable of repeated bending such that the features may be bent into retained shapes or the features retain no general shape, but continuously deform when force is applied. The term "resilient" is used to qualify such flexible features as returning to an initial general shape without permanent deformation. As for the term "semi-rigid," this term is used to connote properties of elements that provide support and are free-standing; however such elements may have some degree of flexibility or resiliency.

It will be understood that unless a term is defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a function is not to be interpreted as a "means" or "step" clause as specified in 35 U.S.C. §112, paragraph 6.

FIGS. 1A-6 show a first embodiment of the hinge for an orthopedic device such as a hinge 100 of a knee brace in an extension position. The hinge 100 supports and simulates movement of the wearer's knee joint and limits flexion and extension of the knee joint with a certain range.

The hinge 100 can include an upper hinge arm 110 that extends from a proximal section to a distal section and a lower hinge arm 112 that extends from a distal section to a proximal section. The hinge arms 110, 112 are arranged to operatively connect the hinge 100 to an orthopedic device. For instance, the distal section of the upper hinge arm 110 can be attached to a first strut of a knee brace and the proximal section of the lower hinge arm 112 can be attached to a second strut of the knee brace.

Each of the hinge arms 110, 112 may be a bar or plate member and may be formed of metal, carbon fiber, plastic, or any other material which would provide sufficient strength to resist deformation during use. As described in more detail below, the distal section of the upper hinge arm 110 and the proximal section of the lower hinge arm 112 can define stop surfaces arranged to engage rotation stops described below.

A long linkage 154 can be pivotally connected at a first location point 114 to the distal section of the upper hinge arm 110 and at second location point 116 to the proximal section of the lower hinge arm 112. The flexion and extension of the hinge 100 as represented by the angle between the upper hinge arm 110 and the lower hinge arm 112 are limited by the rotation stops described below. The long linkage 154 is used to limit further rotation of the hinge arms 110, 112 in a direction.

The long linkage 154 can be a single linkage formed of metal, carbon fiber, plastic and/or any other material which would provide sufficient strength to resist deformation during use of the hinge 100. Because the long linkage 154 is a single linkage rather than multiple linkages or one or more split linkages, it can reduce the overall thickness of the hinge 100.

The long linkage 154 is externally mounted or is mounted on an outer side O of the hinge 100 on the lateral side. The outer side O is defined as being opposed to an inner side I of the hinge that is proximate the anatomy of a wearer of the orthopedic device. This allows the hinge 100 to be more compact and/or streamlined than known hinges because the other components of the hinge 100 need not be spaced apart or oversized to accommodate movement of the long linkage 154.

In the illustrated embodiment, the long linkage 154 can be a cover plate 102, which may have any desired shape, but is shown having a rounded trapezoidal shape. The cover plate 102 can have a distal end portion wider than a proximal end portion of the cover plate 102, the distal end portion providing greater resistance to a bending moment in the hinge 100.

The cover plate 102 can be pivotally connected to the upper hinge arm 110 at the first location point 114 via a first fastener 118 extending through openings in the cover plate 102 and the distal section of the upper hinge arm 110. The cover plate 102 can be pivotally connected to the lower hinge arm 112 at the second connection point 116 via a second fastener 120 extending through openings in the cover plate 102 and the proximal section of the lower hinge arm 112. The first and second connectors 118, 120 can be shoulder rivets or any other suitable connector. The plate 102 can define an arcuate slot 158 for accommodating a stop pin or fastener during movement of the hinge 100 as described in more detail below.

Optionally, the first location point 114 and/or the second location point 116 can include flange bushings 122 and/or bushings 124 (best seen in FIG. 2) extending through the hinge 100, helping to properly align, space, and/or fasten individual components of the hinge 100. This can also help reduce friction between moving components at the location points 114, 116.

The cover plate 102 is arranged to protect the hinge 100 and/or the wearer from pinch points created between the moving components of the hinge 100, making the hinge more durable and safer to wear. Further, because the cover plate 102 is both the long linkage 154 and protects the hinge 100, a separate hinge cover is not needed. This advantageously allows the hinge 100 to include fewer components, which lowers the profile of the hinge 100.

Figure 1B:
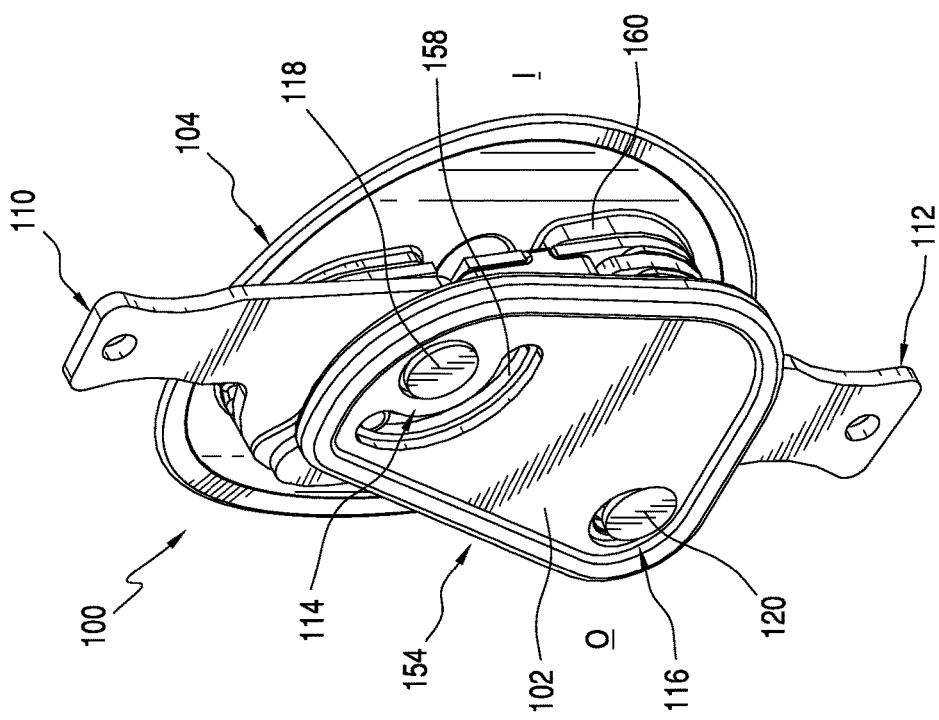
FIG. 1B is a perspective view of the hinge in FIG. 1A according to another embodiment.

The cover plate 102 can have a two-part construction. For instance, the cover plate 102 can have a main body and an overmold or plastic portion covering at least a part of the main body as seen in FIG. 1A. The overmold or plastic part can define one or more lips, helping to shield the anterior and/or posterior side of the hinge 100 from external particles and/or to help prevent foreign material from becoming trapped inside the hinge 100. Alternatively, the cover plate 102A can include a single unitary member as seen in FIG. 1B.

A condyle plate 104 is externally mounted on the medial side of the hinge 100, and along the inner side I of the hinge 100. The condyle plate 104 can be secured to and located adjacent to the second plate 108 (best seen in FIG. 3). The condyle plate 104 is arranged for providing support to the condyle region of the wearer's knee. The condyle plate 104 can be formed of any suitable material such as a resilient material that flexes slightly during movement of the knee or other joint. The condyle plate 104 can have a slightly curved face facing the wearer's knee, allowing the condyle plate 104 to follow the shape of the knee. The face of the condyle plate 104 facing the upper and lower hinge arms 110, 112, can define a raised area 160, providing reinforcement to the short linkage described below.

Figure 2:
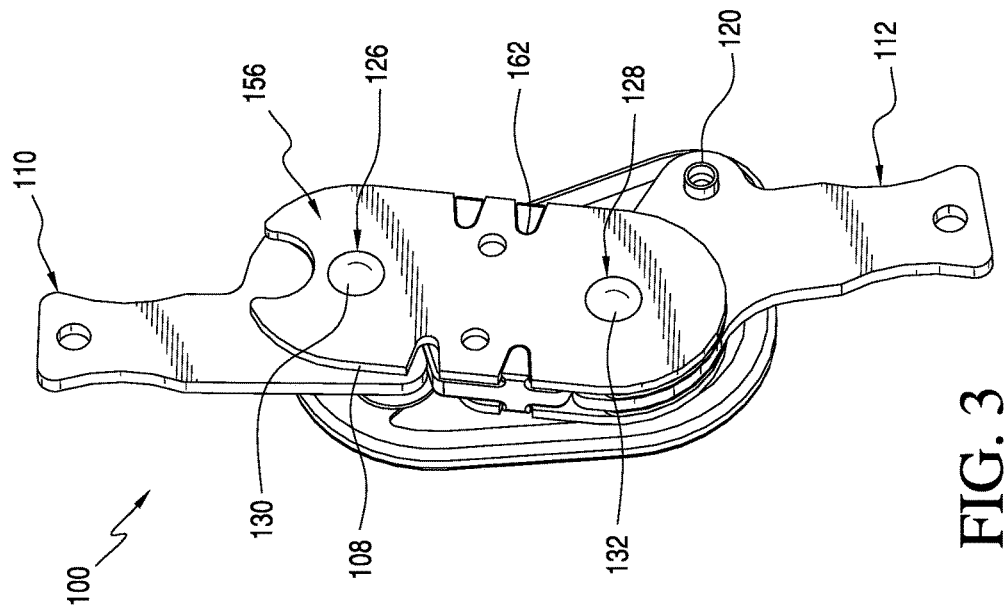
FIG. 2 is a perspective view of the hinge in FIG. 1A with the cover plate hidden for case of reference.
Figure 3:
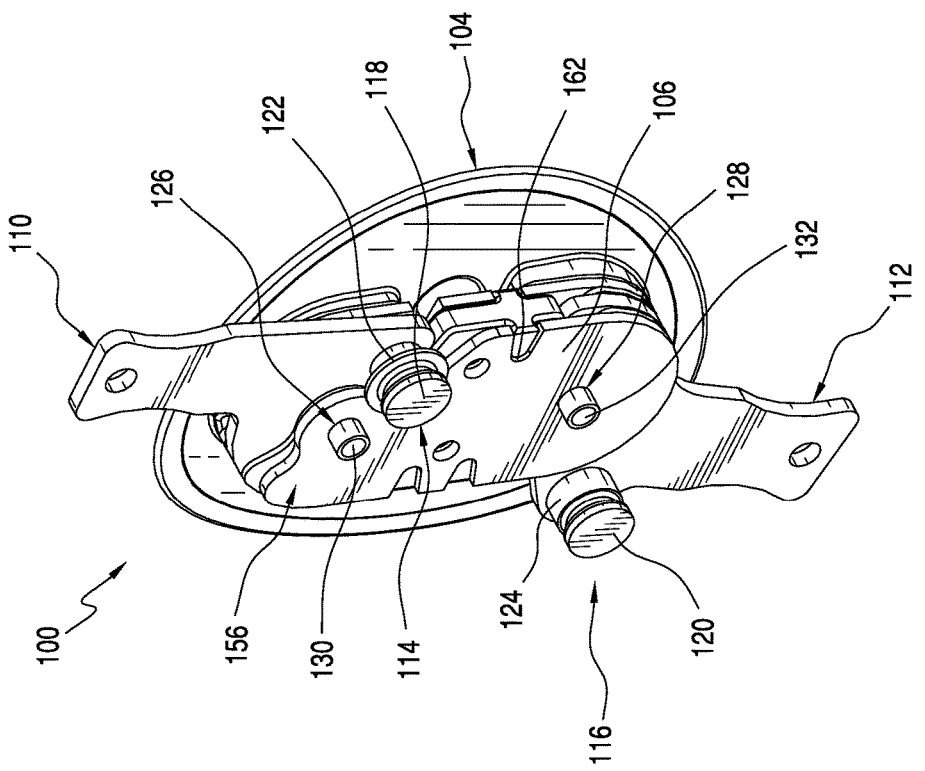
FIG. 3 is a perspective view of the hinge in FIG. 1A with the condyle plate hidden for ease of reference.

As seen in FIGS. 2 and 3, a short linkage 156 can be pivotally connected at a third location point 126 to the distal section of the upper hinge arm 110 and at a fourth location point 128 to the proximal section of the lower hinge arm 112. The short linkage 156 can include a first plate 106 and a second plate 108, each can be formed of metal, carbon fiber, plastic, and/or any other material which would provide sufficient strength to resist deformation during the hinge 100.

The first plate 106 is between the cover plate 102 and the upper and lower hinge arms 110, 112 and the second plate 108 is between the condyle plate 104 and the upper and lower hinge arms 110, 112. Because the first and second plates 106, 108 are generally protected between the cover plate 102 and the condyle plate 104, the likelihood of the plates 106, 108 being damaged by external objects or contact is substantially reduced.

The short linkage 156 can be symmetric regarding the central plane of rotation and advantageously helps distribute the loading of rotation stops described below when a rotational limit has been reached. The hinge 100 is further advantageous since the upper hinge arm 110 and the lower hinge arm 112 are connected to each other by the cover plate 102 and the first and second plates 106, 108, providing additional support in the hinge to resist a bending moment.

The first plate 106 can be a rigid plate or other suitable structure. The first first plate 106 can have any desired shape, but is shown having an irregular geometric shape. The second plate 108 can be a rigid plate or other suitable structure. The second plate 108 is shown having a generally stadium shape, but can have any suitable shape. The first and second plates 106, 108 can be pivotally connected to the upper hinge arm 110 at the third location point 126 via a third connector 130 extending through openings in the short linkages 106, 108 and the distal section of the upper hinge arm 110. The first and second plates 106, 108 can be pivotally connected to the lower hinge arm 112 at the fourth location point 128 via a fourth connector 132 extending through openings in the short linkages 106, 108 and the proximal section of the lower hinge arm 112. The third and fourth connectors 130, 132 can be tubular rivets or any other suitable connector.

Optionally, at least one spacer washer 134 (best seen in FIG. 4) can be at the third and fourth location points 126, 128 between different components of the hinge 100, helping to properly align, space, and/or fasten individual components of the hinge 100. This can also help reduce friction between different components at the location points 126, 128.

As the hinge 100 moves between flexion and extension, the long linkage 154 rotates around the third and fourth location points 126, 128 and around the edges of the first plate 106 and the second plate 108. For instance, the connection of the cover plate 102 at the first location point 114 can rotate around the third connection point 126 and the connection of the cover plate 102 at the second location point 116 can rotate around the fourth location point 128. The third connector 130 fits within the slot 158 defined in the cover plate 102. By extending the third connector 130 through the slot 158, the third connector 130 can help limit further rotation of the hinge arms 110, 112. The lower hinge arm 112 can be wider than the upper hinge arm 110 to provide a larger rotational radius for the distal end of the cover plate 102.

Referring to FIGS. 4 and 5, flexion and extension of the hinge 100 are limited by at least one rotation stop. The rotation stop can include an extension stop 136 and a flexion stop 138. In this embodiment, the limiting of rotation is achieved when the hinge arms 110, 112 abut the rotation stops 136, 138. By using the hinge arms 110, 112 as the contact point with the rotation stops 136, 138, a stronger rotation stopping contact is formed with less opportunity for the hinge arms 110, 112 to slip and allow further undesirable flexion or extension beyond the stopping points. Further, because the rotation stops 136, 138 do not directly contact the long linkage 154, the likelihood of the long linkage 154 being damaged by the rotation stops 136, 138 is reduced.

The tops of the rotation stops 136, 138 have a geometric shape corresponding to the shape of the bottom of the distal end of the upper hinge arm 110. The bottoms of the rotation stops 136, 138 have a geometric shape corresponding to the shape of the top of the proximal end of the lower hinge arm 112. The extension stop 136 can be attached between the first and second plates 106, 108 at a connection point 146 toward the anterior side of the hinge 100. The flexion stop 138 can be attached between the first and second plates 106, 108 at a connection point 148.

The rotation stops 136, 138 can be generally perpendicular to the plane of rotation of the hinge arms 110, 112. Both the rotation stops and the hinge arms can have a thicker configuration. This can increase their strength and can provide a greater normal force contact between the rotation stops 136, 138 and the hinge arms 110, 112.

The thickness of at least one of the rotation stops 136, 138 can be greater than the thickness of at least one of the end surfaces of the hinge arms 110, 112. For instance, the rotation stop can be between about 10 percent and about 100 percent, about 20 percent and about 90 percent, about 30 percent and about 80 percent, or about 20 percent and about 70 percent thicker than the end surface of a hinge arm. It will be appreciated that the rotation stop can be thicker or thinner relative to the end of the hinge arm. This helps prevent the hinge arms 110, 112 from sliding off of the rotation stops 136, 138. The slipping of the hinge arms 110, 112 may cause a bending moment in the hinge 100 that could cause the failure of the hinge 100.

Figure 6:
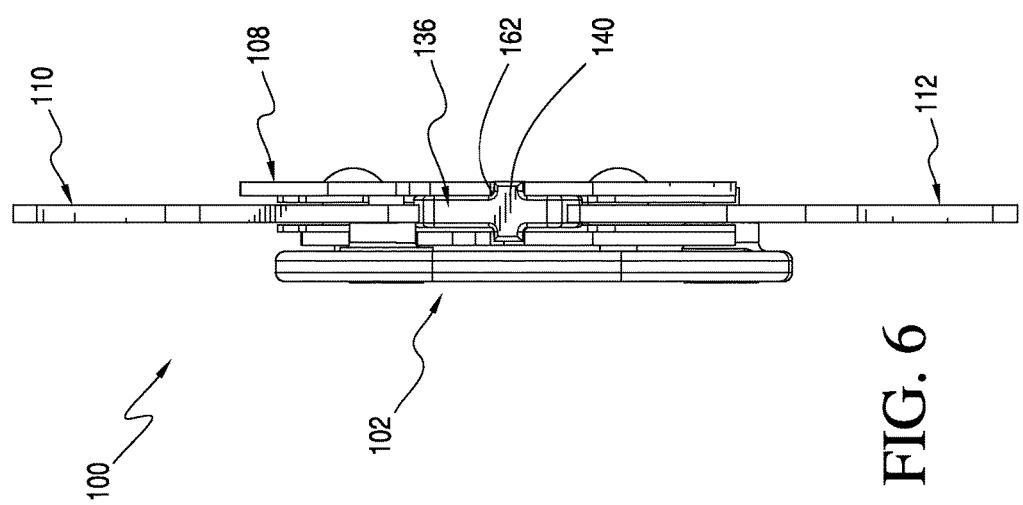
FIG. 6 is a front view of the hinge in FIG. 1A with the condyle plate hidden for ease of reference.

As best seen in FIG. 6, the rotation stops 136, 138 can extend generally the distance between the first and second plates 106, 108. As seen, at least one of the rotation stops 136, 138 can define at least one key 140 arranged to be selectively received within and extend through a corresponding cutout 162 defined in the first and second plates 106, 108. When the upper and lower hinge arms 110, 112 contact the rotation stops 136, 138, the hinge arms 110, 112 load the rotation stops 136, 138. This causes the keys 140 in the cutouts 162 to transfer at least some of the load from the rotation stops to the first and second plates 106, 108, increasing the load capacity of the rotation stops 136, 138. This arrangement also forms another connection between the first and second plates 106, 108, increasing the stiffness of the hinge 100, which helps the hinge 100 resist twisting.

Referring again to FIGS. 4 and 5, the upper surface of the extension stop 136 may have a geometric shape which generally complements or corresponds to a stop surface 142A defined by the distal end of the upper hinge arm 110. The lower surface of the extension stop 138 may have a geometric shape which generally corresponds to a stop surface 144A defined by the proximal end of the lower hinge arm 112. The upper surface of the flexion stop 138 may have a geometric shape which generally corresponds to a stop surface 142B defined by the distal end of the upper hinge arm 110. The lower surface of the flexion stop 138 may have a geometric shape which generally corresponds to a stop surface 144B defined by the proximal end of the lower hinge arm 112. The stop surfaces can be formed from metal, plastic, or another rigid material providing a solid contact surface.

The rotation stops 136, 138 limit rotation of the hinge arms 110, 112 at a predetermined angle defined by the geometric shape and/or thickness of the rotation stops 136, 138. The degree of which rotation is limited may be adjusted by changing the size and/or shape of the extension stop 136 or the flexion stop 138.

The rotation stops 136, 138 can be removably secured to the hinge 100. For instance, pins at the respective connection points 146, 148, can extend between the first and second plates 106, 108 and through the rotation stops 136, 138. The pins can be a two-part screw or any other suitable connector. By securing the rotation stops 136, 138 between the first and second plates 106, 108 with the pins, the control for both flexion and extension is within the hinge 100 as opposed to being along outer portions of the hinge 100. Further, the pins can help support the rotation stops 136, 138 when the hinge arms 110, 112 abut the rotation stops 136, 138.

When a wearer desires to replace and/or repair a rotation stop, the respective pin can be removed from the hinge 100 to easily remove and/or repair the rotation stop as needed. This also allows the degree to which the flexion and/or extension of the hinge 100 is limited to be easily and quickly adjusted by interchanging rotation stops. Alternatively, the rotation stops 136, 138 can be fixedly secured to the hinge 100.

The rotation stops 136, 138 can be provided as a kit including a plurality of rotations stops having a plurality of different geometric and/or degree configurations. Each of the different rotation stops 136, 138 can be secured to the hinge 100 and are removable as needed. One or more of the rotation stops 136, 138 can be a unitary structure or may include a plurality of components.

Friction plates can help control movement between the short linkage 156 and the hinge arms 110, 112. For instance, friction plates 150, 152 can be pivotally attached to the distal end of the upper hinge arm 110 at the third location point 126 and to the proximal end of the lower hinge arm 112 at the fourth location point 128. The friction plates 150, 152 can extend between the rotation stops 136, 138. The friction plates 150, 152 can be made from any suitable material and can exhibit any suitable arrangement.

The friction plate 150 is secured between the first plate 106 and the hinge arms 110, 112. The posterior edge of the friction plate 150 can be curved to generally correspond to the curvature of the rotation stop 138. The anterior edge of the friction plate 150 can be curved to generally correspond to the curvature of the rotation stop 136.

The friction plate 152 is secured between the second plate 108 and the hinge arms 110, 112. The posterior edge of the friction plate 152 can curve to generally correspond to the curvature of the rotation stop 136. The posterior edge of the friction plate 152 can be curved to generally correspond to the curvature of the rotation stop 138. The anterior edge of the friction plate 152 can be curved to generally correspond to the curvature of the rotation stop 136.

The friction plates 150, 152 create a friction surface between the short linkage 156 and the hinge arms 110, 112 during extension and flexion of the hinge 100, helping to control motion of the hinge 100.

It will be appreciated that the hinge 100 is to be regarded as exemplary only, as any hinge is possible. While the plate 102 is described as comprising the long linkage, in other embodiments, the long linkage can comprise one or more bar-like members or any other suitable structure. The long linkage can be positioned in any suitable location on the hinge. In an embodiment, the long linkage can be positioned on an inside of the hinge 100. In yet other embodiments, at least one of the outer plate or the inner plate 108 can be omitted.

Figure 7:
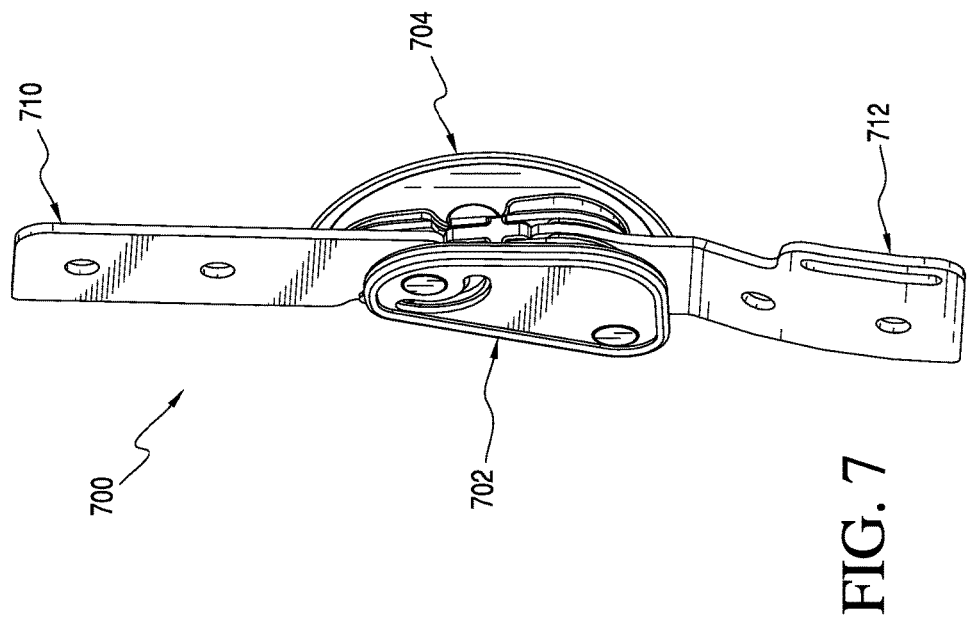
FIG. 7 is a perspective view of a hinge according to another embodiment.

In yet other embodiments, the length of the hinge arms can be changed to adjust the center of rotation of the hinge 100 to create non-natural kinematics to correct for ACL or PCL deficient knees. FIG. 7 illustrates another embodiment of the hinge 700 with longer hinge arms. The cover plate and outer plate are hidden for ease of reference. The hinge 700 is largely similar to the hinge 100, and the same reference numerals are used for components in the hinge 700 similar to those of the hinge 100. The hinge 700 can include a cover plate 702, a condyle plate 704, an outer plate (not shown), an inner plate (not shown), an upper hinge arm 710, a lower hinge arm 712, friction plates (not shown) and rotation stops (not shown). As shown, the hinge arms 710, 712 can be longer than the hinge arms 110, 112. The lower hinge arm 712 can include a portion angled relative to the upper hinge arm 710. In other embodiments, the hinge arms 710, 712 can be shorter than the hinge arms 110, 112. In yet other embodiments, the hinges disclosed can be used with a spring-type center link to adjust the level of correction.

Figure 9:
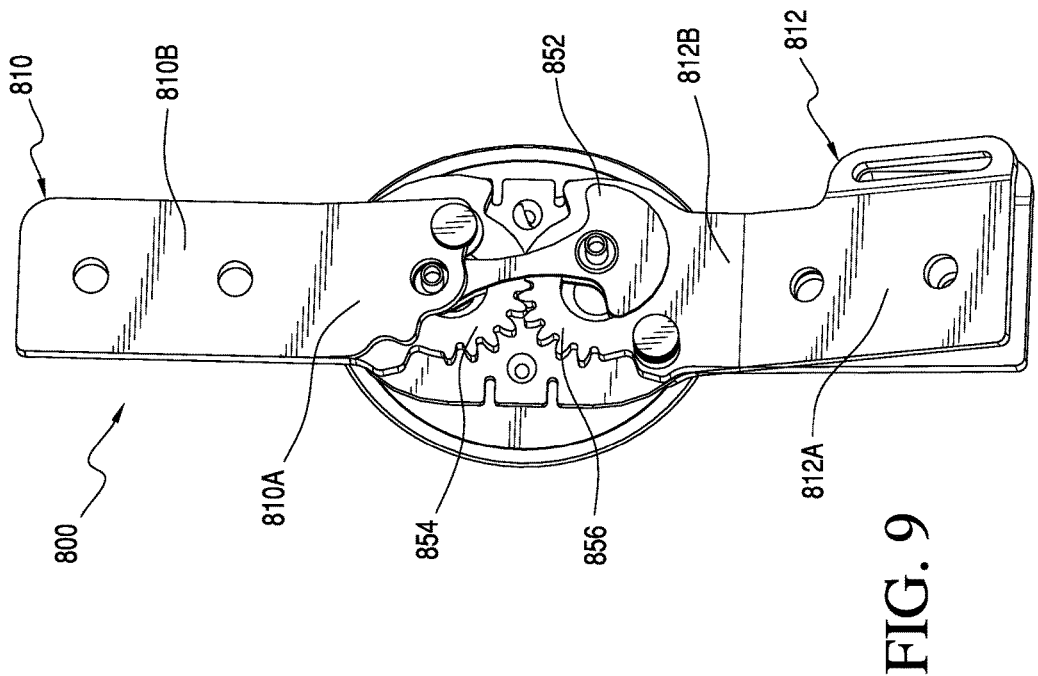
FIG. 9 is another perspective view of the hinge in FIG. 8 with the rotation stops hidden for ease of reference.
Figure 8:
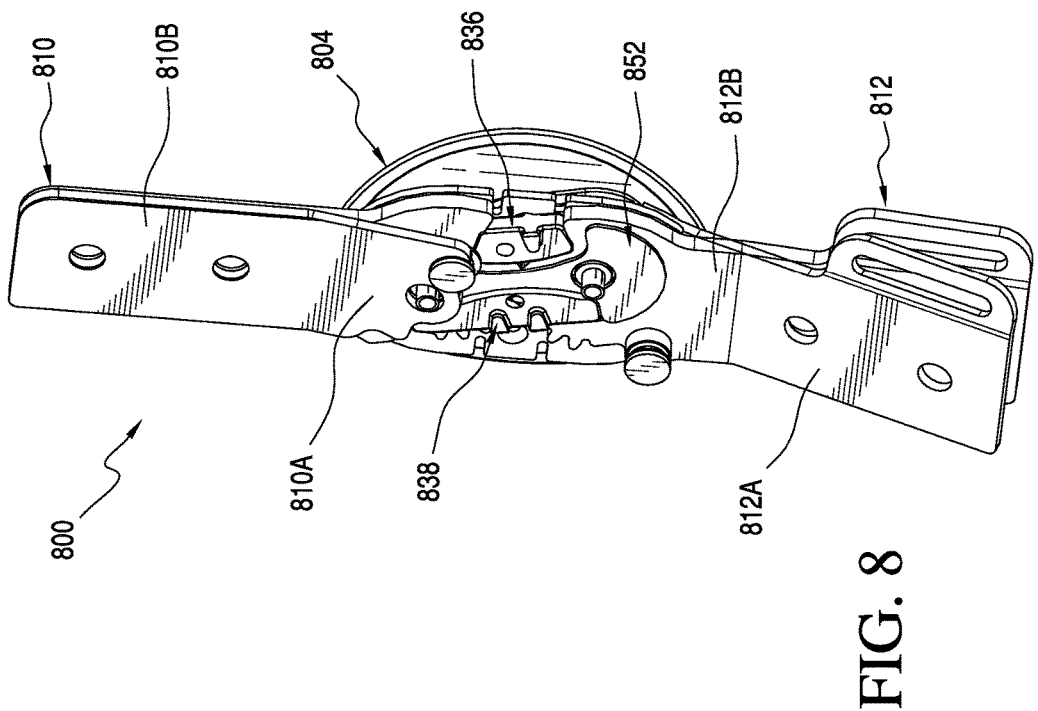
FIG. 8 is a perspective view of a hinge according to another embodiment.

In yet other embodiments, a rack and pinion gear system may be used with the center link and the hinge arms. FIGS. 8 and 9 illustrate another embodiment of a hinge 800 including a rack and pinion gear system. FIG. 8 illustrates the hinge 800 with the cover plate and outer plate hidden for ease of reference. FIG. 9 illustrates the hinge 800 with the cover plate, the outer plate, and the rotation stops hidden to the rack and pinion gear system. Similar to the hinge 100, the hinge 800 can include a cover plate (not shown), a condyle plate 804, and the outer plate are hidden for ease of reference in FIG. 8. The cover plate, condyle plate, outer plate, and rotation stops are hidden for ease of reference in FIG. 9. The hinge 800 is largely similar to the hinges 100 and 800, and the same reference numerals are used for components in the hinge 800 similar to those of the hinges 100 and 700. The hinge 800 can include a cover plate (not shown), an outer plate (not shown), an inner plate (not shown), an upper hinge arm 810, a lower hinge arm 812, friction plates 852, and rotation stops 836, 838 (shown in FIG. 8).

As shown, the upper hinge arm 810 can include a distal portion 810A and a proximal portion 810B and the lower hinge arm 812 can include a distal portion 812A and a proximal portion 812B. The distal portion 810A of the upper hinge arm 810 includes a first plurality of teeth 854 and the proximal portion 812B of the lower hinge arm 812 includes a second plurality of teeth 856. The second teeth 856 of the lower hinge arm 812 are arranged to interact or mesh with the first teeth 854 of the upper hinge arm 810 such that rotation of one of the hinge arms 810, 812 causes and/or controls rotation of the other. This arrangement helps control and/or limit flexion and/or extension of the hinge 800.

While the foregoing embodiments have been described and shown, alternatives and modifications of these embodiments, such as those suggested by others may be made to fall within the scope of the invention. While the hinge has been described in combination with a knee brace, it will be understood that the principles described may be extended to other types of orthopedic and prosthetic devices.

The invention claimed is:

1. A hinge having inner and outer sides opposed to one another, the hinge comprising:
    an upper hinge component;
    a lower hinge component;
    a cover plate pivotally connected at a first location point to the upper hinge component and at a second location point to the lower hinge component;
    first and second plates pivotally connected at a third location point to the upper hinge component and at a fourth location point to the lower hinge component, the first plate positioned between the cover plate and the upper and lower hinge components, and the upper and lower hinge components positioned between the first and second plates, wherein the cover plate is mounted on the outer side of the hinge such that the connection of the cover plate at the first location point rotates around the third location point and the connection of the cover plate at the second location point rotates around the fourth location point; and
    at least one friction plate pivotally attached to the upper hinge component at the third location point and to the lower hinge component at the fourth location point, the at least one friction plate arranged to create a friction surface between the upper and lower hinge components and the first plate or the second plate.

2. The hinge of claim 1, further comprising: a first rotation stop connected at a fifth location point between the first and second plates.

3. The hinge of claim 2, wherein the upper hinge component defines at least one stop surface arranged to directly abut the at least one rotation stop.

4. The hinge of claim 3, wherein the at least one stop surface and the at least one rotation stop have geometrically complementary surface shapes.

5. The hinge of claim 2, wherein the lower hinge component defines at least one stop surface arranged to directly abut the at least one rotation stop.

6. The hinge of claim 5, wherein the at least one stop surface and the at least one rotation stop have geometrically complementary surface shapes.

7. The hinge of claim 2, wherein the at least one rotation stop defines at least one key protruding therefrom arranged to be received within at least one cutout defined by the first plate or the second plate.

8. The hinge of claim 2, wherein the at least one rotation stop is connected to the first and second plates and at least in part transfers a load from the upper and lower hinge components to the first and second plates.

9. The hinge of claim 2, wherein the at least one rotation stop has a first thickness and the upper hinge component has a second thickness that is less than the first thickness.

10. The hinge of claim 2, wherein the at least one rotation stop is an extension stop.

11. The hinge of claim 2, wherein the at least one rotation stop is a flexion stop.

12. The hinge of claim 1, wherein the cover plate defines an arcuate slot arranged to accommodate movement of a connector extending from the third location point.

13. The hinge claim 1, wherein the cover plate comprises a rigid member including a distal end portion that is wider than a proximal end portion of the cover plate.

14. The hinge claim 1, further comprising a condyle plate secured to and located adjacent the second plate.

15. A hinge having inner and outer sides opposed to one another, the hinge comprising:
    an upper hinge component;
    a lower hinge component;
    a long linkage pivotally connected at a first location point to the upper hinge component and at a second location point to the lower hinge component;
    a short linkage pivotally connected at a third location point to the upper hinge component and at a fourth location point to the lower hinge component, the short linkage including a first plate positioned between the long linkage and the upper and lower hinge components and a second plate;
    a first rotation stop connected at a fifth location point between the first and second plates;
    wherein the long linkage is mounted on the outer side of the hinge, the connection of the long linkage at the first location point rotates around the third location point in a first direction, and the connection of the cover plate at the second location point rotates around the fourth location point in a second direction opposite the first direction.

16. The hinge of claim 15, further comprising:
    a second rotation stop connected at a sixth location point between the first and second plates.

17. The hinge of claim 15, wherein the long linkage defines an arcuate slot arranged to accommodate movement of a connector at the third location point.

18. An orthopedic device comprising:
    a hinge having inner and outer sides opposed to one another, the hinge including:
        an upper hinge component;
        a lower hinge component;

a cover plate pivotally connected at a first location point to the upper hinge component and at a second location point to the lower hinge component;

a first and second plate pivotally connected at a third location point to the upper hinge component and at a fourth location point to the lower hinge component, the first plate positioned between the cover plate and the upper and lower hinge components and the upper and lower hinge components positioned between the first and second plates, wherein the cover plate is externally mounted on the hinge and the connection of the cover plate at the first location point rotates around the third location point and the connection of the cover plate at the second location point rotates around the fourth location point; and a first rotation stop connected at a fifth location point between the first and second plates.

19. A hinge having inner and outer sides opposed to one another, the hinge comprising:

an upper hinge component;

a lower hinge component;

a cover plate pivotally connected at a first location point to the upper hinge component and at a second location point to the lower hinge component;

first and second plates pivotally connected at a third location point to the upper hinge component and at a fourth location point to the lower hinge component, the first plate positioned between the cover plate and the upper and lower hinge components, and the upper and lower hinge components positioned between the first and second plates, wherein the cover plate is mounted on the outer side of the hinge such that the connection of the cover plate at the first location point rotates around the third location point and the connection of the cover plate at the second location point rotates around the fourth location point; and a condyle plate secured to and located adjacent the second plate.

* * * * *